(12) United States Patent
Artmann et al.

(10) Patent No.: US 12,214,184 B2
(45) Date of Patent: Feb. 4, 2025

(54) AUTOMATED AND SEMI-AUTOMATED DESIGNS FOR BATTERY CONDITIONING IN A FULLY IMPLANTED LVAD

(71) Applicant: Boston Scientific Scimed, Inc., Maple Grove, MN (US)

(72) Inventors: Joel B. Artmann, Elk River, MN (US); Bo Zhang, Blaine, MN (US); Eric A. Schilling, Ham Lake, MN (US); David I. Siegfried, Edina, MN (US); Stephen M. Nelson, St. Paul, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 921 days.

(21) Appl. No.: 17/114,720

(22) Filed: Dec. 8, 2020

(65) Prior Publication Data
US 2022/0176100 A1  Jun. 9, 2022

(51) Int. Cl.
*A61M 60/873* (2021.01)
*A61M 60/178* (2021.01)
*H02J 7/00* (2006.01)
*H02J 50/10* (2016.01)

(52) U.S. Cl.
CPC ........ *A61M 60/873* (2021.01); *A61M 60/178* (2021.01); *H02J 7/0069* (2020.01); *H02J 7/00712* (2020.01); *A61M 2205/04* (2013.01); *A61M 2205/18* (2013.01); *A61M 2205/3592* (2013.01); *A61M 2205/52* (2013.01); *A61M 2205/8206* (2013.01); *H02J 50/10* (2016.02)

(58) Field of Classification Search
CPC .............. A61M 60/873; A61M 60/178; A61M 2205/04; A61M 2205/18; A61M 2205/3592; A61M 2205/52; A61M 2205/8206; H02J 7/0069; H02J 7/00712; H02J 50/10
USPC ....................................................... 320/106
See application file for complete search history.

(56) References Cited

U.S. PATENT DOCUMENTS

| | | | |
|---|---|---|---|
| 2005/0177198 A1 | 8/2005 | Norton et al. | |
| 2007/0150019 A1 | 6/2007 | Youker et al. | |
| 2009/0248100 A1 | 10/2009 | Vaisnys et al. | |
| 2013/0087624 A1 | 4/2013 | Bertness et al. | |
| 2014/0247155 A1* | 9/2014 | Proud .................... | A61B 5/681 340/870.01 |

(Continued)

FOREIGN PATENT DOCUMENTS

| | | | |
|---|---|---|---|
| CN | 104885327 A | | 9/2015 |
| CN | 109840624 A | * | 6/2019 |

(Continued)

OTHER PUBLICATIONS

International Search Report and Written Opinion of International Application No. PCT/US2021/062104, dated Apr. 4, 2022, 9 pp.

*Primary Examiner* — Suresh Memula
(74) *Attorney, Agent, or Firm* — Seager Tufte & Wickhem, LLP (57) ABSTRACT

In an implanted medical device system, an internal controller, external power transmitter and methods for performing battery conditioning are disclosed. According to one aspect, an internal controller includes processing circuitry configured to cause conditioning of an internal battery of the internal controller responsive to a direction from an external power transmitter in radio communication with the internal controller.

10 Claims, 10 Drawing Sheets

(56) References Cited

U.S. PATENT DOCUMENTS

| | | | | |
|---|---|---|---|---|
| 2018/0366789 A1* | 12/2018 | Petrella | .................. | H02S 40/38 |
| 2019/0255341 A1 | 8/2019 | Buchanan et al. | | |
| 2020/0324126 A1* | 10/2020 | Winstrom | ............. | H02J 50/005 |
| 2022/0193393 A1* | 6/2022 | Artmann | ............. | A61M 60/216 |
| 2022/0226659 A1* | 7/2022 | Zhang | ................ | H02J 7/00034 |

FOREIGN PATENT DOCUMENTS

| | | | | | |
|---|---|---|---|---|---|
| CN | 110506359 A | * | 11/2019 | .............. | B60L 53/11 |
| DE | 112012002922 T5 | | 3/2014 | | |
| EP | 2636426 A1 | * | 9/2013 | ........... | A61B 5/0031 |
| WO | 2011109747 A9 | | 9/2011 | | |

* cited by examiner

FIG. 1

Prior Art

AUTOMATED AND SEMI-AUTOMATED DESIGNS FOR BATTERY CONDITIONING IN A FULLY IMPLANTED LVAD

CROSS-REFERENCE TO RELATED APPLICATION n/a

FIELD

The present technology is generally related to implantable medical devices such as a left ventricular assist device (LVAD), and more particularly to performing battery conditioning of an internal battery.

BACKGROUND

Figure 1:
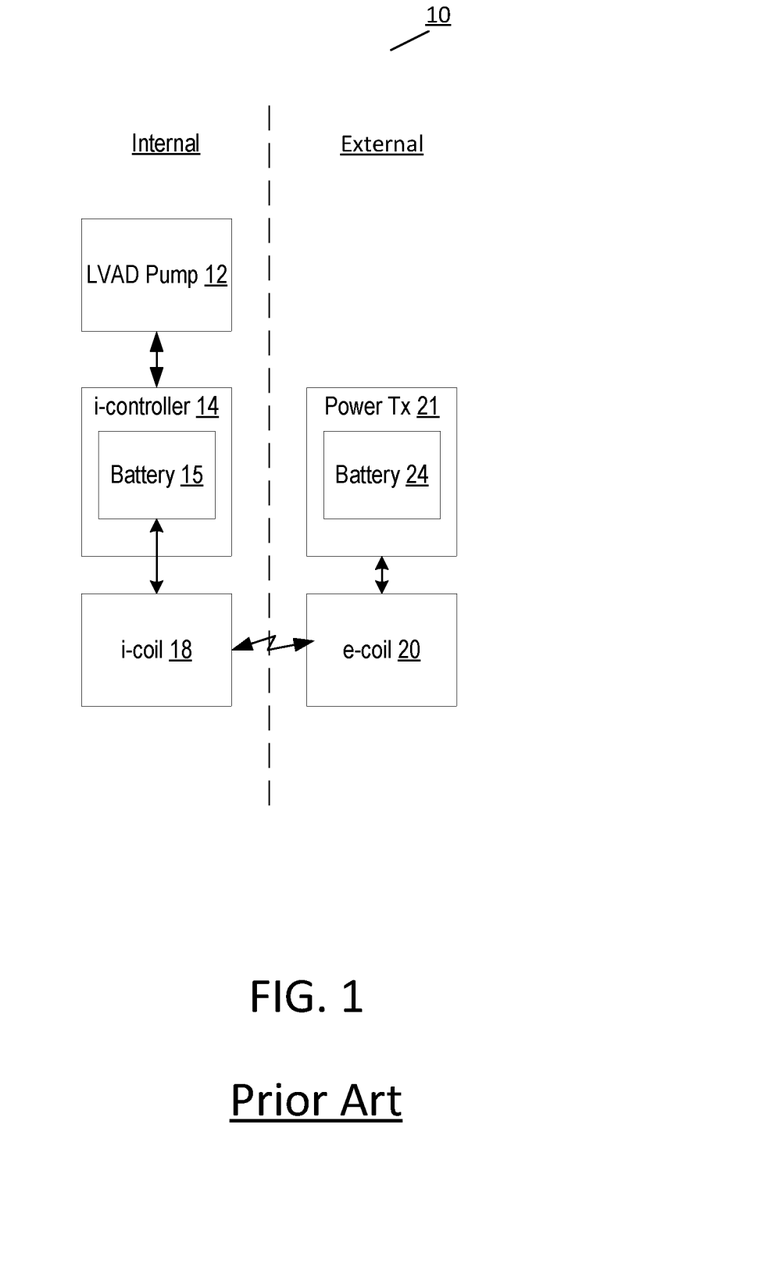
FIG. 1 is a block diagram of an implantable LVAD system.

Referring to FIG. 1, an implantable LVAD system 10 has internal components (in the body of the patient) and external components. The LVAD system 10 may typically include an LVAD pump 12, an implanted controller (i-controller) 14 having an internal battery 15, an implanted internal transcutaneous energy transfer system (TETS) coil (i-coil) 18, an external TETS coil (e-coil) 20 and an external power transmitter 21 with a detachable battery 24. In operation, power is supplied from the external power transmitter 21 to the i-controller 14 via mutual coupling of the coils 18 and 20, in order to charge the internal battery 15 of the i-controller 14 and to power the LVAD pump 12. The coils 18 and 20 transfer power via electromagnetic energy over the air and through the body. The power supplied by the external power transmitter 21 may come from the detachable battery 24 or from a wall outlet, for example.

SUMMARY

The techniques of this disclosure generally relate to performing battery conditioning of an internal battery.

According to one aspect, the present disclosure provides an implanted medical device system, such as a left ventricular assist device (LVAD) system. The implanted medical device system includes an internal controller. The internal controller includes processing circuitry configured to cause conditioning of an internal battery of the internal controller responsive to a direction from an external power transmitter in radio communication with the internal controller.

According to this aspect, in some embodiments, the processing circuitry is further configured to cause discontinuance of a transfer of transcutaneous energy transfer system (TETS) power during the conditioning. In some embodiments, the processing circuitry is further configured to turn off a misalignment alarm during the conditioning. In some embodiments, the processing circuitry is further configured to schedule the conditioning in response to a signal from an external power transmitter. In some embodiments, the processing circuitry is further configured to count a number of failed battery conditioning attempts.

According to another aspect, a method implemented in an internal controller implantable within the body of a patient as part of an implanted medical device system is provided. The method includes causing conditioning of an internal battery of the internal controller responsive to a direction from an external power transmitter in radio communication with the internal controller.

According to this aspect, in some embodiments, the method includes causing discontinuance of a transfer of transcutaneous energy transfer system (TETS) power during the conditioning. In some embodiments, the method also includes turning off a misalignment alarm during the conditioning. In some embodiments, scheduling the conditioning is in response to a signal from an external power transmitter. In some embodiments, the method also includes counting a number of failed battery conditioning attempts.

According to yet another aspect, an external power transmitter of an implanted medical device system is provided. The external power transmitter includes processing circuitry configured to: cause display of messages to a patient to enable the patient to one of select and schedule a time to perform conditioning of a battery of an internal controller implanted in the patient. The processing circuitry is also configured to receive input from the patient that one of selects and schedules a time to perform the conditioning; and cause the internal controller to perform the conditioning at the selected or scheduled time.

According to this aspect, in some embodiments, the processing circuitry is further configured to cause discontinuance of a transfer of transcutaneous energy transfer system (TETS) power during the conditioning. In some embodiments, the processing circuitry is further configured to turn off a misalignment alarm during the conditioning. In some embodiments, the processing circuitry is further configured to count a number of failed battery conditioning attempts. In some embodiments, the processing circuitry is further configured to report when the number of failed battery conditioning attempts exceeds a threshold.

According to another aspect, a method implemented in an external power transmitter of an implanted medical device system is provided. The method includes causing display of messages to a patient to enable the patient to one of select and schedule a time to perform conditioning of a battery of an internal controller implanted in the patient. The method also includes receiving input from the patient that one of selects and schedules a time to perform the conditioning. The method further includes causing the internal controller to perform the conditioning at the selected or scheduled time.

According to this aspect, in some embodiments, the method also includes causing discontinuance of a transfer of transcutaneous energy transfer system (TETS) power during the conditioning. In some embodiments, the method also includes turning off a misalignment alarm during the conditioning. In some embodiments, the method also includes counting a number of failed battery conditioning attempts. In some embodiments, the method also includes reporting when the number of failed battery conditioning attempts exceeds a threshold.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Some embodiments described herein are related to performing battery conditioning. Rechargeable battery capacity fades over time and as a function of a number of recharging cycles of the battery. In order for longevity estimators to account for this capacity fade, battery conditioning cycles are needed periodically in which the current battery capacity is measured. A battery conditioning cycle, or a "Qmax update" consists of phases in which the battery voltage is relaxed, the capacity is depleted by >37%, the voltage is relaxed and the capacity is recharged by >37%. Relaxation of the battery means the battery is not being charged or discharged and the battery voltage settles to a steady state condition. The basic steps of the conditioning cycle may include (1) change battery capacity by a significant amount; (2) relax the battery voltage; (3) measure the battery voltage; (4) change the battery capacity by a significant amount; (5) relax the battery voltage; and (6) measure the battery voltage. Qmax updates are common in commercial electronics with rechargeable batteries (phones). However, accomplishing a Qmax update in a fully implanted LVAD system is complicated by the user interactions and communication mechanisms in the TETS system. Described herein are automated and semi-automated mechanisms for coordinating a Qmax update between an internal controller, an external power transmitter and the patient.

Figure 2:
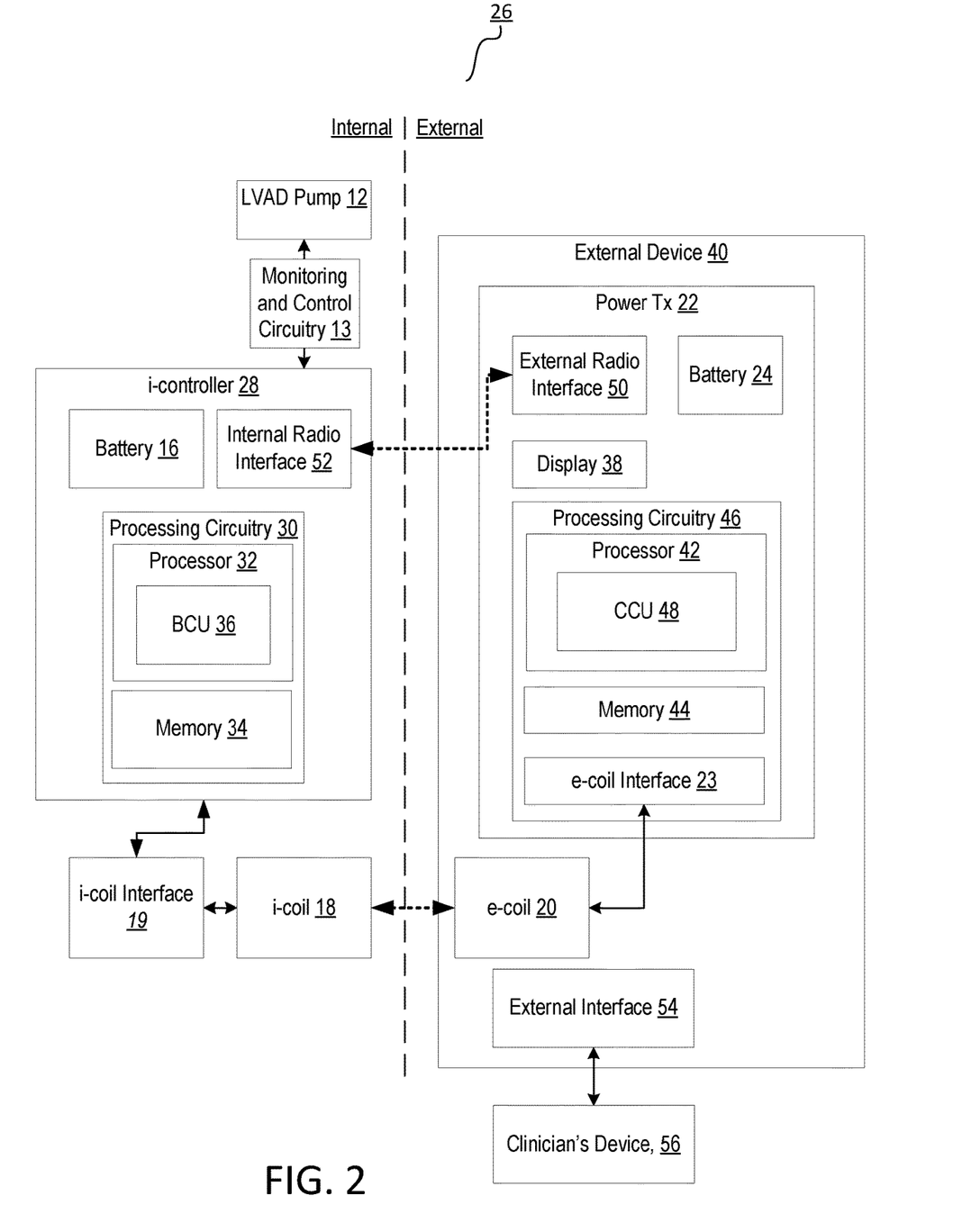
FIG. 2 is a block diagram of an embodiment of an LVAD system that implements a process of performing battery conditioning.

FIG. 2 shows a block diagram of one example configuration of an implanted medical device system 26 having external components such as an external power transmitter 22, and internal components such as an internal controller (i-controller) 28 configured to perform functions described herein. As used herein, the term "implanted medical device system 26" refers to the system that includes both the implanted/implantable components as well as external components described herein.

The i-controller 28 may have processing circuitry 30 which may include a processor 32 and an internal memory 34. The processor 32 may be configured to execute computer instructions stored in the internal memory 34. Those instructions may include instructions to cause the processor to perform some of the processes described in more detail below. The processor 32 may therefore implement a battery conditioning unit (BCU) 36, which serves to perform battery conditioning.

A message or result from the i-controller 28 may be transferred from the i-controller 28 to an external display 38 of an external device 40, which may include a processor 42 and a memory 44 within processing circuitry 46, the external power transmitter 22 and the detachable battery 24, as well as the e-coil 20 in some embodiments. The memory 44 may be configured to store computer instructions to be executed by the processor 42. The processor 42 may implement a conditioning control unit (CCU) 48 configured to control the battery conditioning implemented by the i-controller 28. The external display 38 may be configured to display information received from the i-controller 28.

Electrical communication of signals and power between the internal components of i-controller 28 may be via communication busses and individual electrical conductors not shown in FIG. 2. For example, a multi-conductor address bus and data bus may connect processor 32 with internal memory 34. In some embodiments, an i-coil interface 19 associated with i-coil 18 may be included in the set of internal components making up the implanted medical device system 26. One purpose of i-coil interface 19 may be to modulate the alternating current applied to the i-coil 18 with signals from the i-controller 28 to be transmitted from the i-coil 18 to the e-coil 20 and/or to demodulate signals to be received by the i-coil 18 from the e-coil 20. In some embodiments, a purpose of the i-coil interface 19 is to provide conversion between the alternating current (AC) of the i-coil 18 and direct current (DC) to charge the battery 16.

The power supplied to the i-coil 18 may be adjusted by varying the AC electrical current in the e-coil 20. Some or all functions of the i-coil interface 19 may be included in the i-controller 28 and/or the i-coil 18. In some embodiments, the i-coil 18 and/or i-coil interface 19 may be internal to or considered part of the internal controller 28. Similarly, electrical communication of signals and power between the internal components of external device may be by communication busses and individual electrical conductors not shown in FIG. 2. For example, a multi-conductor address bus and data bus may connect processor 42 with memory 44. In some embodiments, an e-coil interface 23 associated with e-coil 20 may be included in the set of external components making up the implanted medical device system 26. The e-coil interface 23 may include a TETS interface configured to demodulate information signals from the processing circuitry 30 transmitted from the i-coil 18 to the e-coil 20. The e-coil interface 23 may also be configured to couple power from the external power transmitter 22 to the e-coil 20. In some embodiments, the e-coil interface 23 may be two distinct units, one unit for demodulation of signals from the i-controller that are uploaded via the coils 18 and 20, and one unit for coupling power from the external power transmitter 22 to the e-coil 20. In some embodiments, the i-controller 28 may upload information to the external power transmitter 22 via the coils 18 and 20, but the power transmitter does not download information to the i-controller 28 via the coils 18 and 20.

In some embodiments, the internal components of the implanted medical device system 26 may include monitoring and control circuitry 13. A purpose of monitoring and control circuitry 13 may include monitoring speed and temperature, for example, of the LVAD pump 12. Another purpose of the monitoring and control circuitry 13 may include controlling the speed of the LVAD pump 12. Another purpose of the monitoring and control circuitry 13 may include monitoring the temperature of the i-controller 28, the i-coil 18 and/or the implanted battery 16. In some embodiments, some or all of the monitoring and control circuitry 13 may be incorporated into the LVAD pump 12 and/or the i-controller 28. In some embodiments, some or all of the functions performed by the monitoring and control circuitry 13 may be performed by the processing circuitry 30. Thus, in some embodiments, the monitoring and control circuitry 13 may include one or more temperature sensors embedded in the LVAD pump 12, the i-controller 28, the i-coil 18 and/or implanted battery 16. Information obtained from and/or about the LVAD pump 12, such as speed and temperature, may be sent to the external device 40 to be displayed by external display 38. Note that although an LVAD pump 12 is shown, other internal devices may be powered and controlled by the i-controller 28 instead of or in addition to an LVAD pump 12.

The various internal components making up the LVAD system may be grouped into one or more separate housings. Similarly, the various external components making up the LVAD system may be grouped into one or more separate housings. Further, some of the components shown and described as being internal to the i-controller 28 may be instead, external to i-controller 28 in some embodiments. Similarly, some of the components shown and described as being internal to the external device 40 may be instead, external to external device 40, in some embodiments. Note further that some of the functions performed by processor 32 may be performed instead by processor 42.

Note that transfer of information from the external device 40 to the internal memory 34, and vice versa, may be by wireless radio frequency (RF) transmission (over the air and through the body when the i-controller 28 is implanted). Accordingly, in some embodiments, the external device 40 includes an external radio interface 50 and the i-controller 28 includes an internal radio interface 52. In some embodiments, the external radio interface 50 and the internal radio interface 52 are RF transceivers having both an RF receiver for receiving information wirelessly and an RF transmitter for transmitting information wirelessly. Such RF transceivers may be Bluetooth and/or Wi-Fi compliant, for example. In some embodiments, the RF receiver and RF transmitter within the external device 40 or within the i-controller 28 are integrated into one unit, whereas in some embodiments, they could be physically separate units.

Also, information may be communicated to the i-controller 28 from the external power transmitter 22 via the coils 18 and 20, by modulating a parameter of power transmission, such as modulating the frequency of the transmitted power, or by modulating a parameter of the i-coil interface 19, for example, by modulating a tuning capacitance of the i-coil interface 19 or by modulating the load level of the i-controller and/or the i-coil interface 19.

The external device 40 could be a patient's external device that has an external interface 54 which provides an interface between the external device 40 and a clinician's device 56. The clinician's device might, for example, have a USB port and interface 54 might include a USB port, so that a USB cable may connect the two ports. The clinician's device 56 may read data from the external device 40 and write information and control signaling to the external device 40, in some embodiments. In the alternative to a wireline connection, the interface 54 could include or be a radio interface.

Figure 3:
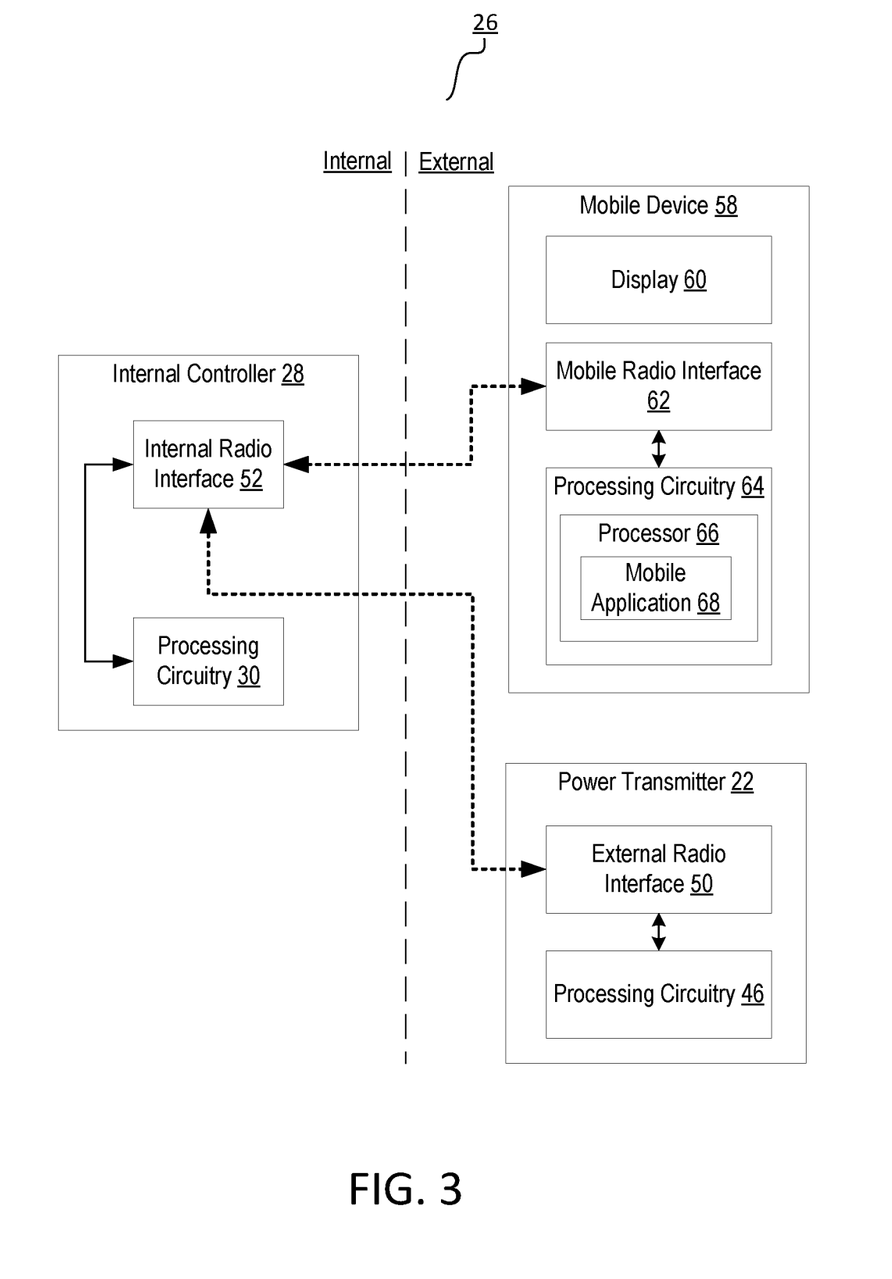
FIG. 3 is a block diagram of an implanted medical device system that includes a mobile device with a mobile application in wireless communication with an internal controller of the implanted medical device.

FIG. 3 is a block diagram of an implanted medical device system 26 that includes a mobile device 58 with a mobile application 68 in wireless communication with the i-controller 28. The mobile device 58 may be a mobile phone or other mobile digital device that can process information and communicate wirelessly with the i-controller. Accordingly, the mobile device 58 has a display 60, a mobile radio interface 62, processing circuitry 64, processor 66 which runs the mobile application 68. The radio interfaces 50, 52 and 62 may be Bluetooth Low Energy compatible radio interfaces, and the i-controller 28 may be a peripheral device responsible for advertising, while the mobile device 58 and the external power transmitter 22 may operate as master or central devices responsible for scanning and issuing connection requests.

Communication from the i-controller 28 to the external power transmitter 22 enables display on external display 38 of implanted device information such as pump data and alarm indications. The i-controller 28 may exchange, via the radio interfaces 50 and 52, diagnostic and log file data with the external power transmitter 22. The i-controller 28 may receive programming commands from an external device such as the clinician's device 56 or mobile device 58. Further, communication from the i-controller 28 to the mobile device 58, via the radio interfaces 52 and 62, enables remote monitoring in cases where the mobile device 58 is connected to the Internet, and enables the display 60 to display information about the state of the implanted portion of the implanted medical device system 26 such as, for example, remaining battery runtime. In some embodiments, the internal radio interface 52 may only communicate with the external radio interface 50 and the mobile radio interface 62 one at a time. In some embodiments, when the i-controller 28 is not engaged in a communication session with an external device, such as external power transmitter 22 or mobile device 58, the i-controller 28 may advertise continually to enable rapid reestablishment of the wireless connection between the i-controller 28 and the external power transmitter 22 or mobile device 58. Conversely, either one or both of the external power transmitter 22 or mobile device 58 may scan for such advertisements. In some embodiments, at least some of the functionality described herein with respect to the external power transmitter 22 can be performed by the mobile device 58.

Figure 4:
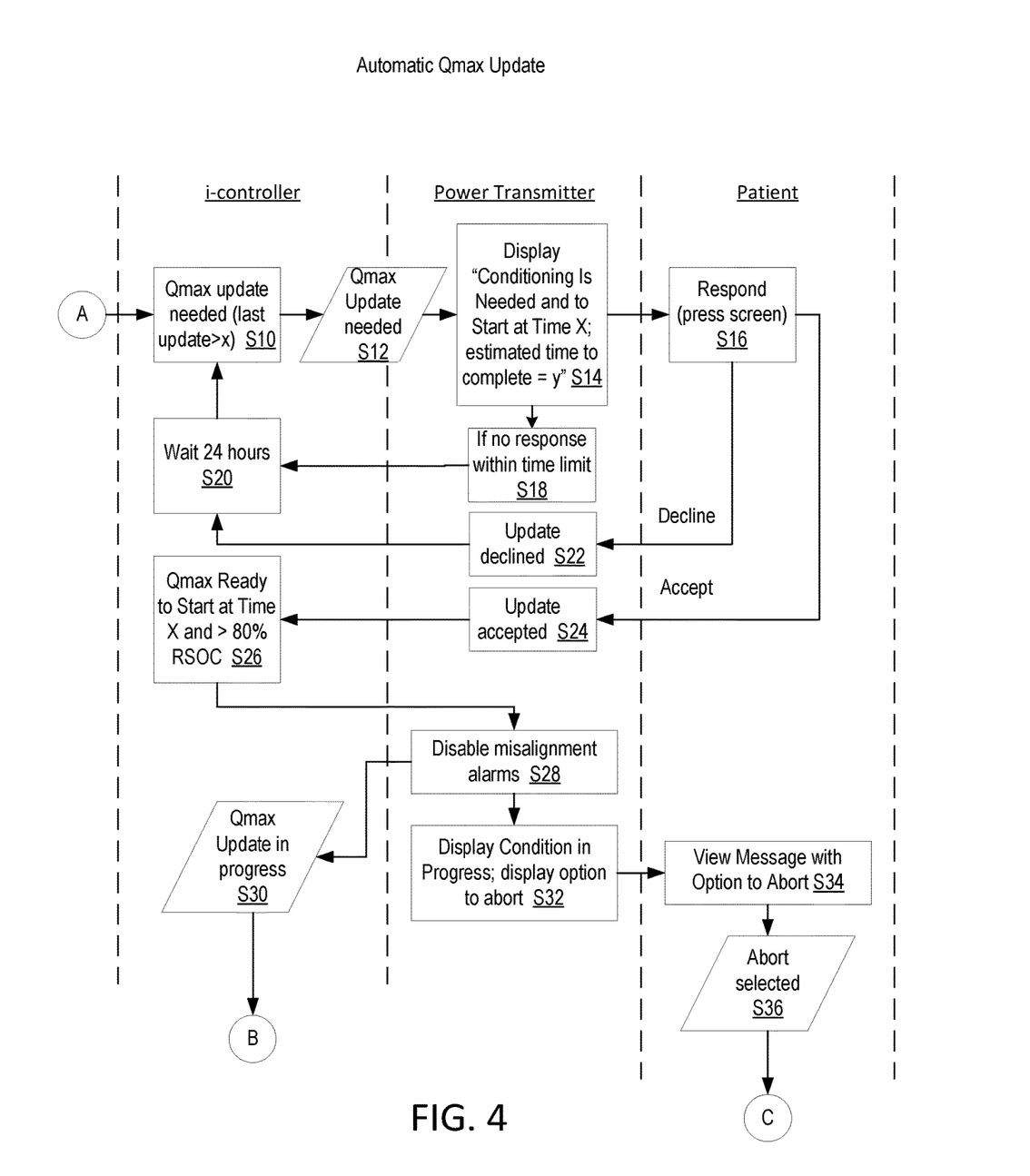
FIG. 4 is a flowchart of an example process for automatic Qmax updates.
Figure 5:
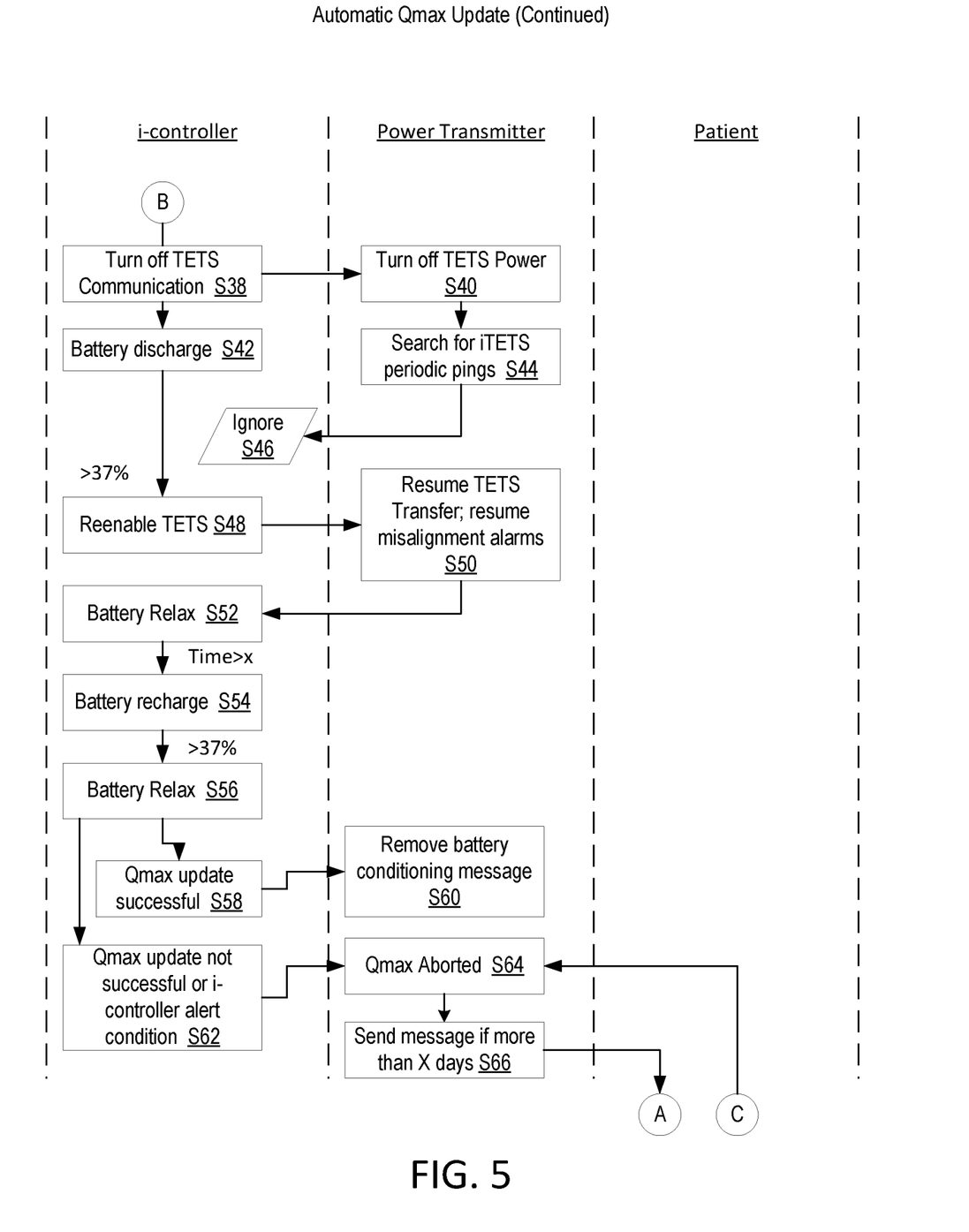
FIG. 5 is a continuation of the flowchart of FIG. 4.
Figure 6:
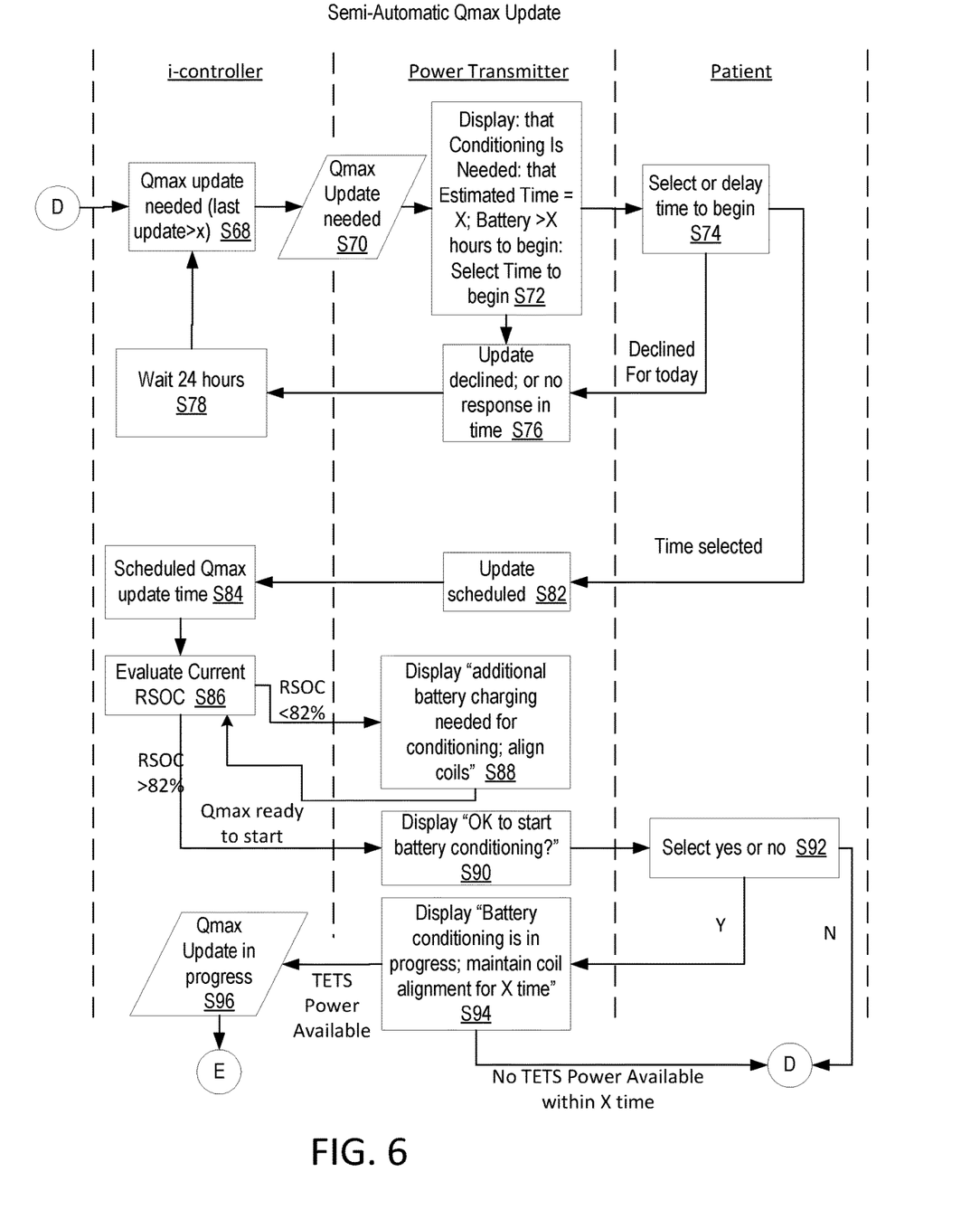
FIG. 6 is a flowchart of an example process for semi-automatic Qmax updates.
Figure 7:
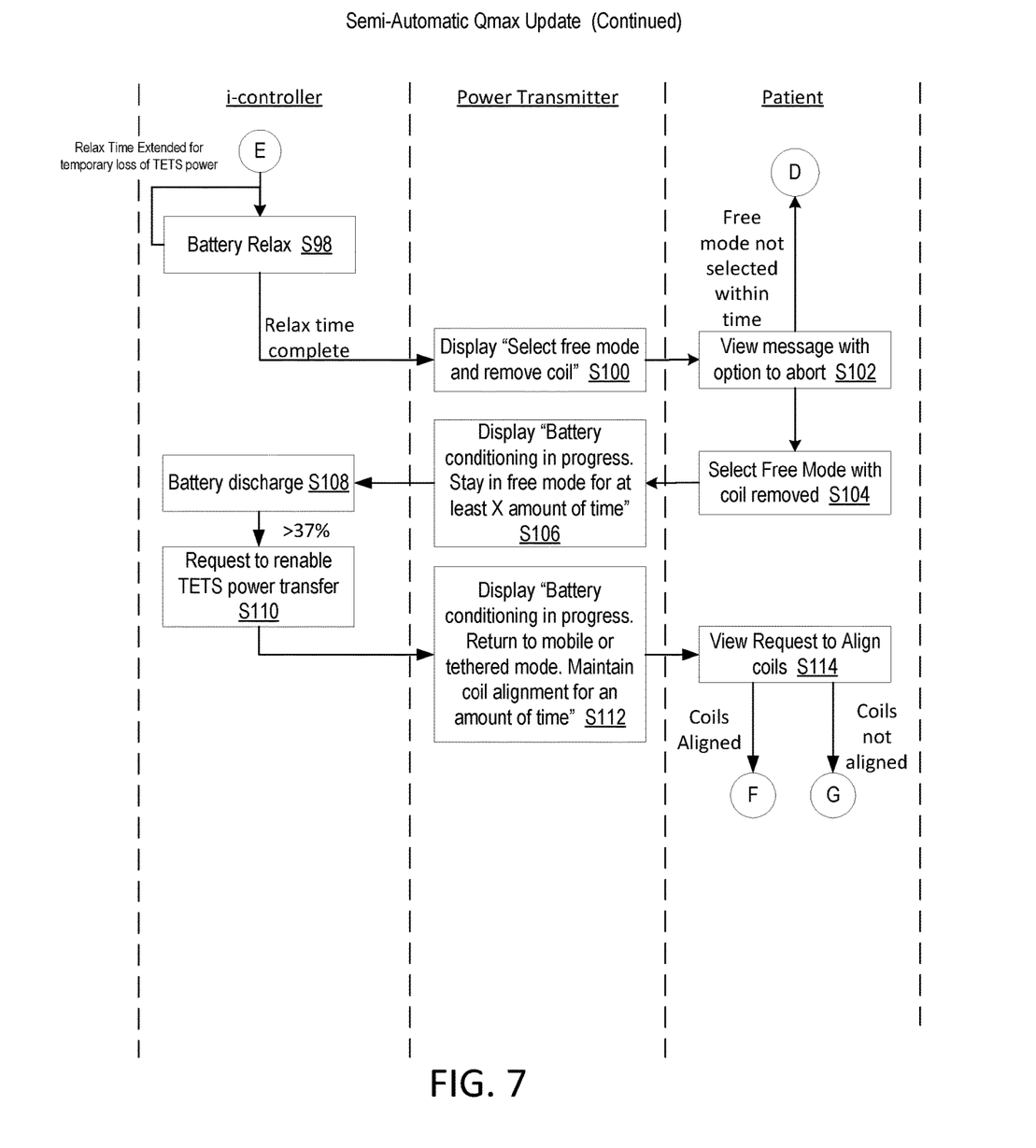
FIG. 7 is a continuation of the flowchart of FIG. 5.
Figure 8:
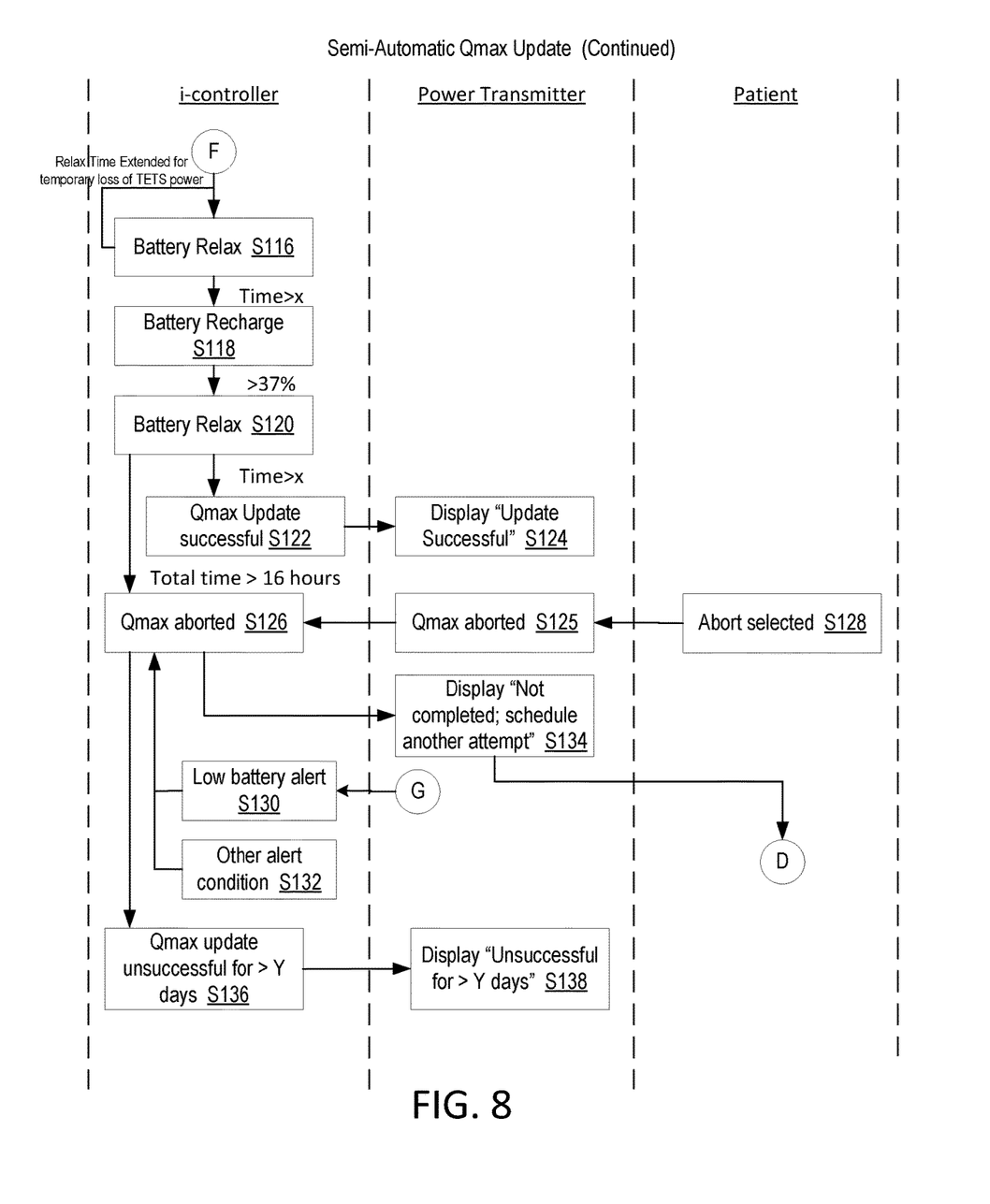
FIG. 8 is a continuation of the flowcharts of FIGS. 6 and 7.

FIGS. 4 and 5 illustrate an automatic process for performing battery conditioning. FIGS. 6-8 illustrate a semi-automatic process for performing battery conditioning. A key difference between the automatic process and the semi-automatic process is a level of involvement of the patient. In the automatic process, TETS power transfer is discontinued automatically, whereas in the semi-automatic process, the patient must remove the external coil from proximity of the internal coil.

FIG. 4 is a flowchart of a process jointly performed by the i-controller 28 and the external power transmitter 22. Starting at Block S10, the i-controller 28 determines that a Qmax update is desired or needed. This may be based on an amount of time since the last Qmax update. When a Qmax update is needed or desired (Block S12), the external power transmitter 22 is signaled and responds by displaying on the external display 38 that conditioning of the internal battery 16 is needed and will start at a particular time, X. The external display 38 is also caused to display an estimated time to complete the Qmax update (Block S14). The patient may respond by depressing a button illustrated on the external display 38, the selecting indicating whether the user accepts or declines the invitation to perform a Qmax update (Block S16). If the patient does not respond by the time limit for response displayed by the external display 38 (Block S18), the external power transmitter 22 signals the i-controller 28 to wait for 24 hours, for example, (Block S20), before starting a next Q-max update process (Block S10). If the invitation to perform a Qmax update is declined by the patient (Block S22), then the i-controller 28 is signaled by the external power transmitter 22 to wait 24 hours, for example, (Block S20), before starting a next Qmax update process (Block S10). Note that in addition to displaying messages, the external power transmitter 22 may emit an audible alert when, for example, there is low battery, power transfer fault or misaligned TETS coils 18 and 20.

When the patient accepts the invitation to perform a Qmax update (Block S24), the external power transmitter 22 may signal to the i-controller 28 that the Qmax update is to start at a time X and when the relative state of charge (RSOC) of the internal battery is greater than some value such as 80% for example (Block S26). The external power transmitter 22 may also disable misalignment alarms that might otherwise sound when the i-coils 18 and 20 are misaligned (Block S28). The i-controller 28 then begins to perform a Qmax update (Block S30). The process continues at point B of FIG. 5. Also, the external power transmitter 22 may cause the external display 38 to display that the battery conditioning is in progress and further display an option to abort (Block S32). The patient may view this message (Block S34) and if abort is selected (Block S36), the process continues at point C of FIG. 5.

Continuing at point B of FIG. 5, the i-controller 28 turns off TETS communication (Block S38). The external power transmitter 22 turns off TETS power transfer (Block S40). The i-controller 28 allows the internal battery 16 to discharge (Block S42). The external power transmitter 22 may search for periodic pings from the i-controller 28 (Block S44). The i-controller 28 may ignore pings from the external power transmitter 22 (Block S46). When the battery discharges to less than some predetermined value or by some percent such as 37% for example, Then TETS power transfer is reenabled (Block S48). The external power transmitter 28 may resume TETS power transfer and resume misalignment alarms (Block S50). The i-controller 28 allows the internal battery 16 to relax (Block S52) for a specified period of time. Then, the i-controller allows the internal battery 16 to recharge (Block S54) to a predetermined level or by some percent such 37% capacity change. The i-controller 28 may then allow the internal battery 16 to relax again (Block S56). When the Qmax update is successful (Block S58) then a battery conditioning message may be removed from a display by the external display 38 (Block S60). When the Qmax update is not successful or there is an i-controller alert condition (Block S62), then the Qmax update process may be aborted (Block S64). Also, when the process continues from point C of FIG. 4, the Qmax update process may be aborted (Block S64). If more than a predetermined number of days, for example, have expired since the last Qmax update, then a message may be displayed by the external display 38 or be sent to a clinician or programmer that the Qmax has not been updated since the last update. The message may state the number of days since the last Qmax update (Block S66). The process may continue at point A of FIG. 4.

FIGS. 6-8 depict a flowchart of an example process for performing Qmax updates on an internal battery 16 of an i-controller 28. The process is performed jointly by the i-controller 28 and the external power transmitter 22, with input from the patient. Beginning at Block S68 of FIG. 6, a determination is made by the i-controller 28 that a Qmax update is needed or desired. When a Qmax update is needed or desired (Block S70), the external power transmitter 22 causes the external display 38 to display that conditioning is needed, the estimated time to complete a Qmax update, that the internal battery 16 must have at least a first duration of time of charge, and a message that requests the patient to select a time to begin the Qmax update (Block S72). The patient may then select or delay a time to perform the Qmax update (Block S74). If the update is declined or there is no response from the patient within a certain amount of time (Block S76), then the i-controller 28 may be directed to wait 24 hours or some other period of time (Block S78). If the patient declines to schedule a Qmax update, then the external power transmitter 22 returns to Block S76. If, on the other hand, the patient selects a time to perform the Qmax update, the external power transmitter 22 schedules the Qmax update at the time selected by the patient (Block S82). Note that the patient may be instructed or encouraged to select a time for Qmax update when the internal battery 16 is likely to be highly charged, in some embodiments. The time selected by the patient may be sent from the external power transmitter 22 to the i-controller 28, which schedules the Qmax update (Block S84). The i-controller 28 evaluates a current relative state of charge (RSOC) (Block S86). If the RSOC is less than a predetermined amount such as 82% for example, the external power transmitter 22 may display that the additional battery charging is needed to start battery conditioning and that the patient should align the coils 18 and 20 (Block S88). The process then returns to Block S86. On the other hand, if RSOC is greater than a predetermined amount such as 82% for example, the i-controller 28 indicates to the external power transmitter 22 that a Qmax update is ready to start. In response, the external power transmitter 22 may display a message to the patient asking if the patient is OK with starting battery conditioning (Block S90). In response to this message, the patient may select yes or no (Block S92). If the patient elects not to proceed with the battery conditioning (Qmax update) then the process continues at point D, Block S68. If the patient elects to proceed with the Qmax update, the external power transmitter 22 may display that battery conditioning is in progress and the coil alignment should be maintained for a period of time (Block S94). If there is no TETS power transfer within a predetermined time, the process continues at point D, Block S68. If TETS power is available, the i-controller 28 may enter a Qmax update process (Block S96) which is shown starting at point E of FIG. 7.

Continuing at point E of FIG. 7, the i-controller 28 allows the battery to relax (Block S98). When there is a temporary loss of TETS power, the relaxation time may be extended. When a relaxation time is complete, the external power transmitter 22 may display a message to the patient to select a free mode and remove the e-coil 20 (Block S100). The patient may view this message (Block S102), which may be displayed with an option to abort (Block S102). If the free mode is not selected by the patient within a period of time, the process continues at point D of FIG. 6. If, on the other hand, the free mode is selected and the e-coil 20 is removed from proximity of the i-coil 18 (Block S104), the external power transmitter 22 displays a message that battery conditioning is in progress and instructing the patient to remain in the free mode for a specified period of time (Block S106). The i-controller 28 causes the internal battery 16 to discharge (Block S108). When a capacity change of the internal battery 16 exceeds a predetermined value such as 37% for example, the i-controller sends a request to the external power transmitter 22 to restore TETS power transfer (Block S110). The external power transmitter 22 displays that battery conditioning is in progress, advises the patient to return to a tethered mode and maintain coil alignment for an amount of time (Block S112). The patient may then view the request to align the coils (i.e., return to the tethered mode)

(Block S114). When the coils 18 and 20 are aligned, the process continues at point F in FIG. 8 and if the coils 18 and 20 are not aligned, the process continues at point G of FIG. 8.

Continuing at point F of FIG. 8, the internal battery 16 is relaxed (Block S116). The relaxation time of the internal battery 16 may be extended when there is a temporary loss of TETS power. After a relaxation time that exceeds or reaches a predetermined level, the internal battery 16 may recharge (Block S118). When the internal battery 16 charge increases by a predetermined amount such as for example 37%, the internal battery 16 may relax (Block S120). After another relaxation time, if the Qmax update is successful (Block S122), as determined by the i-controller 28, for example, the external power transmitter 22 may display a message that the update was successful (Block S124). On the other hand, if the total time of the Qmax update steps S116-S120, exceeds some predetermined time such as 16 hours for example, the Qmax update may be aborted (Block S126). In the alternative, or in addition, if the patient elects to abort the Qmax update (Block S128), the external power transmitter 22 may acknowledge the aborting (Block S125) and instruct the i-controller 28 to abort the Qmax update (Block S126). Other events that may cause the aborting of the Qmax update include a low battery (Block S130) or other i-controller alert conditions (Block S132). When the Qmax update is aborted, the external power transmitter 22 may display that the Qmax update was not completed and inviting the patient to schedule another attempt (Block S134). The process may then continue to point D of FIG. 6. If no Qmax update has been successful for a predetermined number of days, for example, (Block S136) and the Qmax update is aborted, the external power transmitter 22 may display a message that the Qmax update has been unsuccessful for so many days, for example (Block S138).

Figure 9:
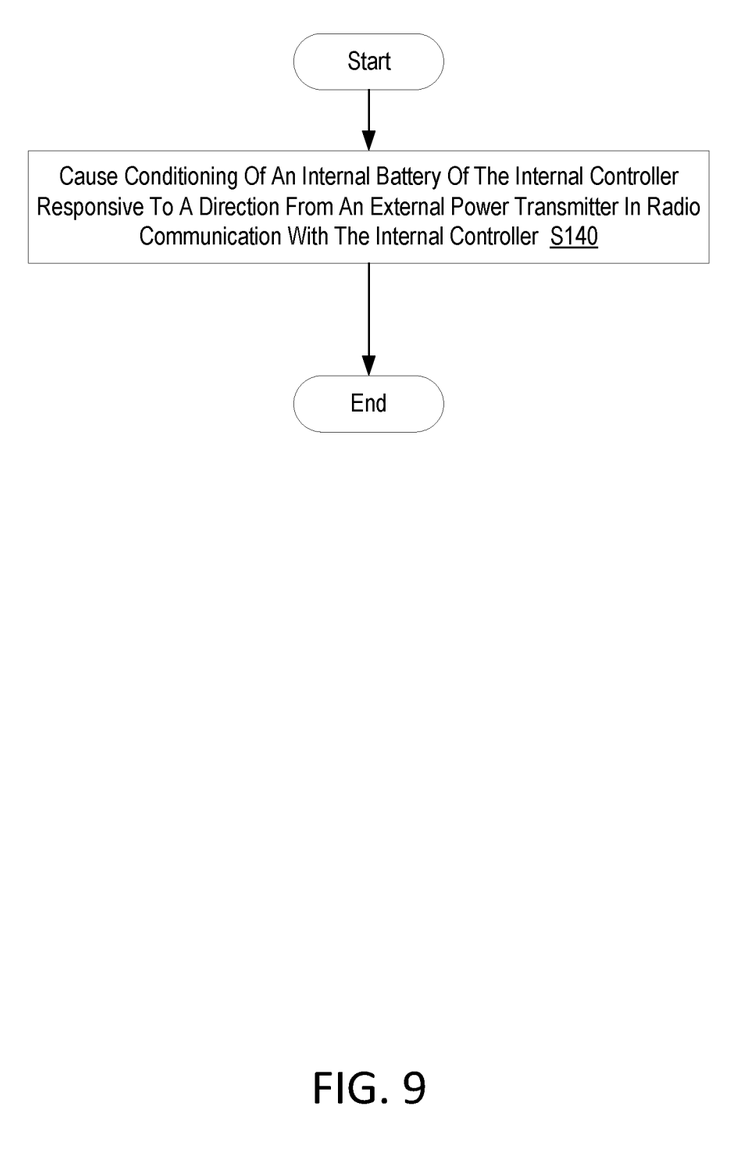
FIG. 9 is a flowchart of an example process in an internal controller according to principles set forth herein.

FIG. 9 is a flowchart of an exemplary process implemented in an internal controller 28 of an implantable medical device for performing internal battery conditioning. The process may be implemented by the processing circuitry 30 of the i-controller 28. The process includes causing conditioning of the internal battery 16 of the i-controller 28 responsive to a direction from an external power transmitter 22 in radio communication with the i-controller 28 (Block S140).

Figure 10:
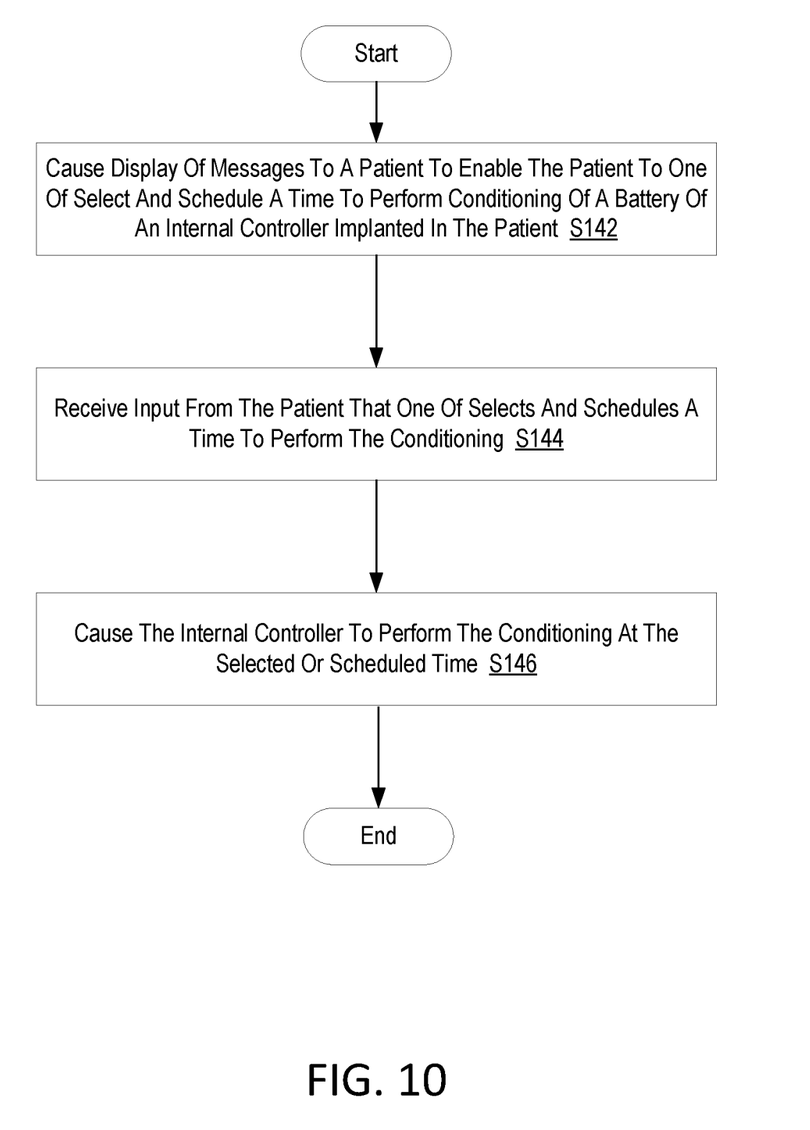
FIG. 10 is a flowchart of an example process in an external power transmitter according to principles set forth herein.

FIG. 10 is a flowchart of a process implemented in an external power transmitter 22 of an implantable medical device for performing conditioning of an internal battery 16 implanted in a patient. The process may be performed by the processing circuitry 46 of the external power transmitter 46, as well as the external radio interface 50. The process includes causing display of messages to a patient to enable the patient to one of select and schedule a time to perform conditioning of a battery 16 of an internal controller 28 implanted in the patient. (Block S142). The process also includes receiving input from the patient that one of selects and schedules a time to perform the conditioning (Block S144). The process further includes causing the internal controller 28 to perform the conditioning at the selected or scheduled time (Block S146).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media and memory may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An external power transmitter of an implanted medical device system, the external power transmitter comprising processing circuitry configured to:
   cause display of messages to a patient to enable the patient to schedule a later time to perform conditioning of a battery of an internal controller implanted in the patient;
   receive input from the patient that selects a scheduled a time to perform the conditioning; and
   cause the internal controller to perform the conditioning at the scheduled time.

2. The external power transmitter of claim 1, wherein the processing circuitry is further configured to cause discontinuance of a transfer of transcutaneous energy transfer system (TETS) power during the conditioning.

3. The external power transmitter of claim 2, wherein the processing circuitry is further configured to turn off a misalignment alarm during the conditioning.

4. The external power transmitter of claim 1, wherein the processing circuitry is further configured to count a number of failed battery conditioning attempts.

5. The external power transmitter of claim 4, wherein the processing circuitry is further configured to report when the number of failed battery conditioning attempts exceeds a threshold.

6. A method implemented in an external power transmitter of an implanted medical device system, the method comprising:

causing display of messages to a patient to enable the patient to schedule a later time to perform conditioning of a battery of an internal controller implanted in the patient;

receiving input from the patient that selects a scheduled time to perform the conditioning; and causing the internal controller to perform the conditioning at the scheduled time.

7. The method of claim 6, further comprising causing discontinuance of a transfer of transcutaneous energy transfer system (TETS) power during the conditioning.

8. The method of claim 7, further comprising turning off a misalignment alarm during the conditioning.

9. The method of claim 6, further comprising counting a number of failed battery conditioning attempts.

10. The method of claim 9, further comprising reporting when the number of failed battery conditioning attempts exceeds a threshold.

* * * * *